(12) United States Patent
Jasti et al.

(10) Patent No.: US 9,162,939 B2
(45) Date of Patent: Oct. 20, 2015

(54) CARBON NANOHOOPS AND METHODS OF MAKING

(71) Applicant: The Regents of the University of California, Oakland, CA (US)

(72) Inventors: Ramesh Jasti, Boston, MA (US); Carolyn Bertozzi, Berkeley, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 14/621,340

(22) Filed: Feb. 12, 2015

(65) Prior Publication Data

US 2015/0152022 A1    Jun. 4, 2015

Related U.S. Application Data

(62) Division of application No. 13/888,273, filed on May 6, 2013, now Pat. No. 8,987,538, which is a division of application No. 12/955,211, filed on Nov. 29, 2010, now Pat. No. 8,461,403.

(60) Provisional application No. 61/266,667, filed on Dec. 4, 2009.

(51) Int. Cl.
| C07C 13/273 | (2006.01) |
|---|---|
| C07C 1/22 | (2006.01) |
| C07C 15/14 | (2006.01) |
| C07C 41/16 | (2006.01) |
| C07C 41/30 | (2006.01) |
| C07C 43/192 | (2006.01) |
| C07C 43/21 | (2006.01) |
| C07C 41/01 | (2006.01) |
| C07F 5/02 | (2006.01) |

(52) U.S. Cl.
CPC . *C07C 1/22* (2013.01); *C07C 15/14* (2013.01); *C07C 41/01* (2013.01); *C07C 41/16* (2013.01); *C07C 41/30* (2013.01); *C07C 43/192* (2013.01); *C07C 43/21* (2013.01); *C07F 5/025* (2013.01); *C07C 2103/92* (2013.01); *C07C 2523/04* (2013.01)

(58) Field of Classification Search
USPC ............................................. 585/24, 25, 26
See application file for complete search history.

(56) References Cited

PUBLICATIONS

Bertozzi; Journal of the American Chemical Society (communications) 2008, 130, 17646-17647; published online Dec. 4, 2008.*
Bertozzi et al; Journal of the American Chemical Society (communications) 2008, 130, 17646-17647.
Bertozzi et al; Journal of American Chemical Society, Dec. 4, 2008, 130, pp. 17646-17647.
Jagadeesh et al; Journal of Molecular Modeling; 2000, 6, pp. 226.
Takaba et al., "Selective Synthesis of [12] Cycloparaphenylene," 2009, Angew. Chem. Int. Ed., 48, pp. 6112-6116.

* cited by examiner

*Primary Examiner* — Sudhakar Katakam
*Assistant Examiner* — Pancham Bakshi
(74) *Attorney, Agent, or Firm* — Kilpatrick Townsend & Stockton LLP

(57) ABSTRACT

The present invention provides cycloparaphenylene compounds, their macrocyclic precursors, and methods for making the compounds. The cycloparaphenylene compounds can be used to prepare armchair carbon nanotubes.

6 Claims, 2 Drawing Sheets

*Reagents and conditions: (a) i. nBuLi, THF, −78 °C, ii. benzoquinone; (b) i. NaH, THF, 0 °C, ii. MeI, 0 °C to rt; (c) i. nBuLi, THF, −78 °C, ii. isopropyl pinacol borate (Bpin), −78 °C; (d) Pd(PPh$_3$)$_4$, Cs$_2$CO$_3$, toluene/methanol (10:1), 80 °C.

*Solids (amorphous) under ambient light:*

9-ring      12-ring      18-ring

*Solids irradiated with 365 nm light:*

9-ring      12-ring      18-ring

*Chloroform solutions (approximately 1 mg/ml) irradiated with 365 nm light:*

CARBON NANOHOOPS AND METHODS OF MAKING

CROSS-REFERENCES TO RELATED APPLICATIONS

This application is a divisional of U.S. application Ser. No. 13/888,273, filed May 6, 2013, which is a divisional of U.S. application Ser. No. 12/955,211, filed Nov. 29, 2010, which claims priority to U.S. Provisional Application No. 61/266,667, filed Dec. 4, 2009, all of which are incorporated in their entirety herein for all purposes.

STATEMENT AS TO RIGHTS TO INVENTIONS MADE UNDER FEDERALLY SPONSORED RESEARCH AND DEVELOPMENT

This invention was made with Government support under Grant No. DE-AC02-05CH11231, awarded by the U.S. Department of Energy. The Government has certain rights in this invention.

BACKGROUND OF THE INVENTION

Carbon nanotubes (also herein referred to as CNTs) are very small tube-shaped structures essentially having a composition of a graphite sheet in a tubular form. Carbon nanotubes have interesting and potentially useful electrical and mechanical properties and offer potential for various uses in electronic devices. Carbon nanotubes also feature extremely high electrical conductivity, very small diameters (much less than 100 nanometers), large aspect ratios (i.e. length/diameter ratios) (greater than 1000), and a tip-surface area near the theoretical limit (the smaller the tip-surface area, the more concentrated the electric field, and the greater the field enhancement factor). These features make carbon nanotubes ideal candidates for electron field emitters, white light sources, lithium secondary batteries, hydrogen storage cells, transistors, and cathode ray tubes (CRTs).

Generally, there are three methods for manufacturing carbon nanotubes. The first method is the arc discharge method, which was first discovered and reported in an article by Sumio Iijima, entitled "Helical Microtubules of Graphitic Carbon" (Nature, Vol. 354, Nov. 7, 1991, pp. 56-58). The second method is the laser ablation method, which was reported in an article by T. W. Ebbesen et al., entitled "Large-scale Synthesis of Carbon Nanotubes" (Nature, Vol. 358, 1992, pp. 220). The third method is the chemical vapor deposition (CVD) method, which was reported in an article by W. Z. Li, entitled "Large-scale Synthesis of Aligned Carbon Nanotubes" (Science, Vol. 274, 1996, pp. 1701).

In order to use the carbon nanotubes more widely and more effectively, it is necessary to implement a controlled growth of the carbon nanotubes with desired structural parameters. An alternative method of preparing carbon nanotubes is to use a seed or template form of the CNT to be prepared and grow the CNT from the seed or template. Based on the seed or template selected, only the specific CNT would be prepared. For example, using a macrocycle of cycloparaphenylene as a template, armchair CNTs can be prepared under suitable conditions. The cycloparaphenylenes are the smallest unit of an armchair CNT and, thus, can be used as seeds or templates to prepare large quantities of carbon nanotubes having specific electronic properties. What is needed, however, is a method of making the cycloparaphenylenes. Surprisingly, the present invention meets this and other needs.

BRIEF SUMMARY OF THE INVENTION

In some embodiments, the present invention provides cycloparaphenylene compounds of formula I:

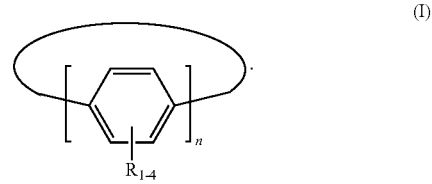

Each R group of formula I can independently be hydrogen, $C_{1-6}$ alkyl, $C_{3-8}$ cycloalkyl or aryl. Alternatively, two R groups on adjacent carbons can be combined with the atoms to which each is attached to form a $C_{5-8}$ cycloalkyl or an aryl. In addition, subscript n of formula I can be an integer from 6 to 30.

In another embodiment, the present invention also provides compounds of formula II:

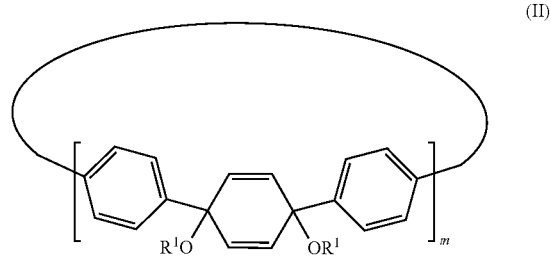

Each $R^1$ of formula II can be hydrogen, $C_{1-6}$ alkyl, $C_{1-6}$ heteroalkyl, $C_{3-8}$ cycloalkyl, heterocycloalkyl, aryl or heteroaryl. Moreover, subscript m can be an integer from 2 to 10.

In other embodiments, the present invention provides compounds of formula III:

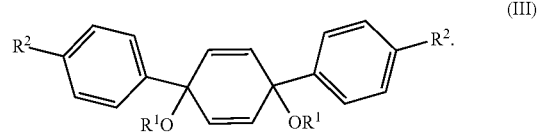

Each $R^1$ of formula III can be as defined above. Moreover, each $R^2$ can independently be a halogen or a boronate.

In some other embodiments, the present invention provides a method of preparing a compound of formula I. In formula I, each R can be hydrogen, and subscript n can be an integer of 6, 9, 12, 15, 18, 21, 24, 27 or 30. The method includes the step of contacting a reducing agent and a compound of formula II, where each $R^1$ can be hydrogen, $C_{1-6}$ alkyl, $C_{1-6}$ heteroalkyl, $C_{3-8}$ cycloalkyl, heterocycloalkyl, aryl or heteroaryl, and subscript m can be an integer from 2 to 10. Thus, the compound of formula I is prepared.

In still other embodiments, the present invention provides a method of preparing a compound of formula IIa:

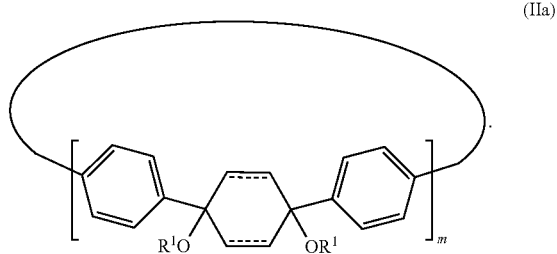

(IIa)

In formula IIa, each $R^1$ can independently be hydrogen, $C_{1-6}$ alkyl, $C_{1-6}$ heteroalkyl, $C_{3-8}$ cycloalkyl, heterocycloalkyl, aryl or heteroaryl. Each dashed line of formula IIa can optionally be a bond, and subscript m can be an integer from 2 to 10. The method of preparing a compound of formula IIa includes contacting a plurality of compounds of formula IIIa:

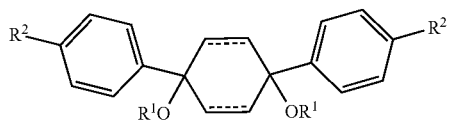

(IIIa)

where each $R^2$ can independently be a halogen or a boronate. Thus, the compound of formula IIa is prepared.

DETAILED DESCRIPTION OF THE INVENTION

I. General

Figure 1:
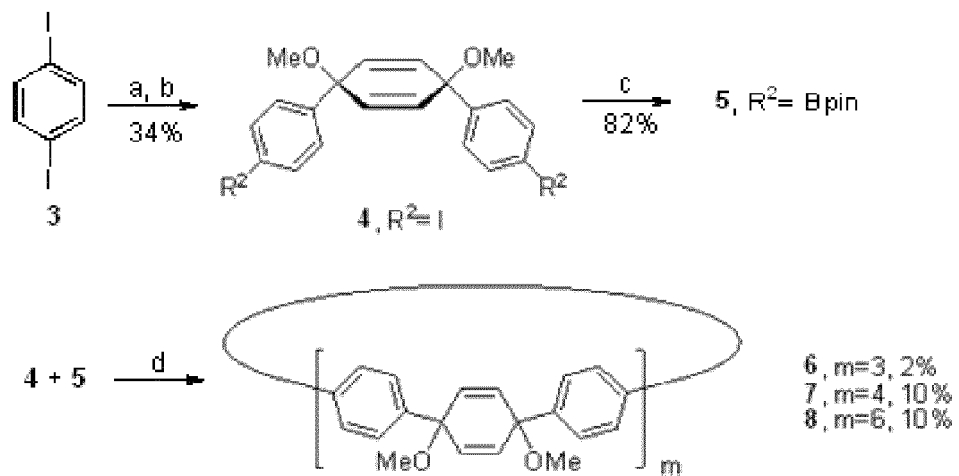
FIG. 1 shows preparation of macrocyclic precursors of the present invention by first reacting 1,4-diiodobenzene with benzoquinone, followed by alkylation of the hydroxyl groups with methyliodide, to afford compound 4, a compound of formula III. Some of compound 4 is then reacted with a borate to convert the iodide groups to boronate 5. Compounds 4 and 5 are then coupled to form cyclic precursors including compounds 6, 7 and 8.
Figure 2:
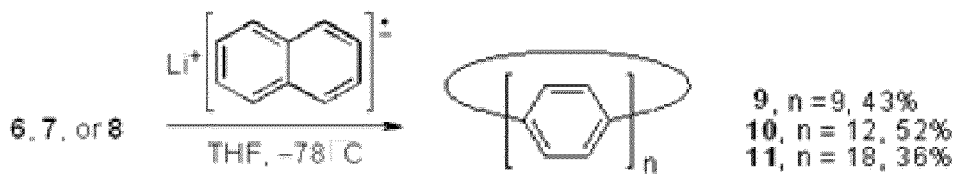
FIG. 2 shows preparation of cycloparaphenylenes 9, 10 and 11 via aromatization of compounds 6, 7 and 8 using lithium naphthalenide as a one-electron reductant.
Figure 3:
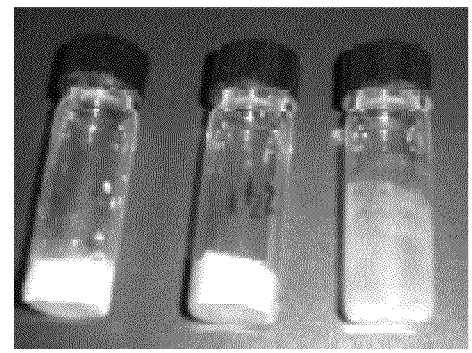
FIG. 3 shows images of compounds 9 (9-membered ring), 10 (12-membered ring) and 11 (18-membered ring) in the solid (amorphous) form, solids of 9, 10 and 11 irradiated with light at 365 nm, and solutions of 9, 10 and 11 irradiated with light at 365 nm.
Figure 3:
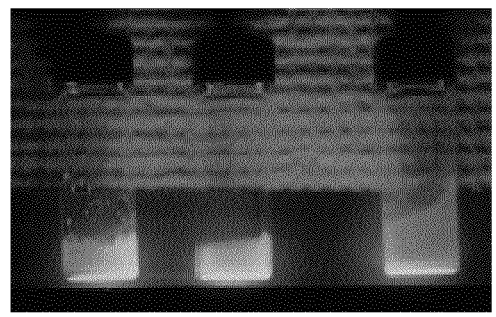
Figure 3:
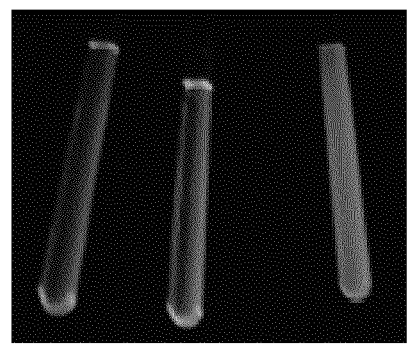

The present invention provides cycloparaphenylenes and methods for making. Also provided are the corresponding macrocyclic precursors and methods for making. The cycloparaphenylenes are the smallest fragment of an armchair (metallic) carbon nanotube and are useful as templates for the preparation of carbon nanotubes, as dyes, and as sensors for the complexation of other agents.

II. Definitions

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc.

Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched) one or two carbon atoms.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', ═N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")═NR"", —NR—C(NR'R")═NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl groups is typically monovalent, but can be divalent, such as when the alkenyl group links two moieties together.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl groups is typically monovalent, but can be divalent, such as when the alkynyl group links two moieties together.

As used herein, the term "alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

As used herein, the term "cycloalkyl" refers to a saturated or partially unsaturated, monocyclic, fused bicyclic or bridged polycyclic ring assembly containing from 3 to 12 ring atoms, or the number of atoms indicated Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, etc.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, flouromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

As used herein, the term "halogen" refers to fluorine, chlorine, bromine and iodine.

As used herein, the term "boronate" refers to esters of boronic acid. Boronates include compounds of the formula R"—B(OR')$_2$, where R' is linked to the compound of interest and R" can be alkyl, heteroalkyl, cycloalkyl, heterocycloalkyl, aryl or heteroaryl, as described above. Alternatively, the two R" groups can be combined to form a heterocycloalkyl group. Exemplary boronates include, but are not limited to, pinacol boronate.

As used herein, the term "contacting" refers to the process of bringing into contact at least two distinct species such that they can react. It should be appreciated; however, the resulting reaction product can be produced directly from a reaction between the added reagents or from an intermediate from one or more of the added reagents which can be produced in the reaction mixture.

As used herein, the term "reducing agent" refers to an agent capable of reducing another compound. The reducing agent can be a metal, an organic compound, or a complex of a metal and an organic compound. For example, the reducing agent can be lithium naphthalenide. Other reducing agents include one-electron reductants capable of transferring an electron from a metal to an organic compound, forming a radical anion that then performs the reduction.

Examples of one-electron reductants include lithium or sodium naphthalenide. Other reducing agents include Pd/H$_2$ and electrochemical reduction methods.

As used herein, the term "alkali metal" refers to the following elements of the periodic Li, Na, K, Rb and Cs.

As used herein, the term "quinone" refers to compounds of the following formula:

where the compounds are optionally substituted. Quinones useful in the present invention include, but are not limited to, benzoquinone, naphthoquinone and anthraquinone.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

III. Compounds

The present invention provides cycloparaphenylene compounds useful for the preparation of armchair carbon nanotubes. In some embodiments, the cycloparaphenylene compounds can have from 6 to 30 paraphenylene rings and can be substituted or unsubstituted. In other embodiments, the compounds can have formula I:

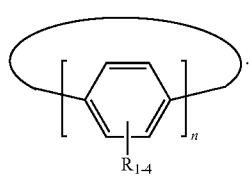

(I)

In formula I, each R can independently be hydrogen, halogen, $C_{1-6}$ alkyl, $C_{1-6}$ haloalkyl, $C_{1-6}$ heteroalkyl, $C_{2-6}$ alkenyl, $C_{2-6}$ alkynyl, $C_{1-6}$ haloalkoxy, —OR$^a$, —C(O)R$^a$, —C(O)OR$^a$, —OC(O)R$^a$, —C(O)NR$^a$R$^b$, —NR$^a$R$^b$, —SR$^a$, —N(R$^a$)C(O)R$^b$, —N(R$^a$)C(O)OR$^b$, —N(R$^a$)C(O)NR$^a$R$^b$, —OP(O)(OR$^a$)$_2$, —S(O)$_2$OR$^a$, —S(O)$_2$NR$^a$R$^b$, —CN, cycloalkyl, heterocycloalkyl, aryl or heteroaryl, wherein each R$^a$ and R$^b$ is independently hydrogen, $C_{1-6}$ alkyl, cycloalkyl, heterocycloalkyl, aryl or heteroaryl. Alternatively, R$^a$ and R$^b$ are combined with the atoms to which each is attached to from a heterocycloalkyl or a heteroaryl. In addition, two R groups on adjacent carbons of formula I can be combined with the atoms to which each is attached to form a $C_{5-8}$ cycloalkyl or an aryl. Moreover, the compounds of formula I can be of any suitable size. For example, subscript n can be from 6 to more than 100.

In some other embodiments, each R group of formula I can independently be hydrogen, $C_{1-6}$ alkyl, $C_{3-8}$ cycloalkyl or aryl. Alternatively, two R groups on adjacent carbons of formula I can be combined with the atoms to which each is attached to form a $C_{5-8}$ cycloalkyl or an aryl. In addition, subscript n of formula I can be an integer from 6 to 30. In still other embodiments, each R group is hydrogen.

In other embodiments, subscript n can be 6, 9, 12, 15, 18, 21, 24, 27 or 30. In still other embodiments, subscript n can be 9, 12 or 18. In yet other embodiments, each R can be hydrogen and subscript n can be 9, 12 or 18.

The present invention also provides compounds of formula II:

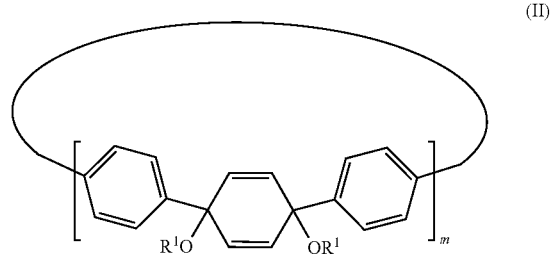

(II)

In some embodiments, each R$^1$ of formula II can independently be hydrogen, $C_{1-6}$ alkyl, $C_{1-6}$ haloalkyl, $C_{1-6}$ heteroalkyl, $C_{2-6}$ alkenyl, $C_{2-6}$ alkynyl, —C(O)R$^a$, —C(O)OR$^a$, —C(O)NR$^a$R$^b$, —P(O)(OR$^a$)$_2$, cycloalkyl, heterocycloalkyl, aryl or heteroaryl, wherein R$^a$ and R$^b$ are as defined above. In other embodiments, each R$^1$ of formula II can be hydrogen, $C_{1-6}$ alkyl, $C_{1-6}$ heteroalkyl, $C_{3-8}$ cycloalkyl, heterocycloalkyl, aryl or heteroaryl. Moreover, subscript m can be an integer from 2 to 10. In some other embodiments, each R$^1$ of formula II can be $C_{1-6}$ alkyl. In still other embodiments, each R$^1$ of formula II can be methyl. In yet other embodiments, subscript m of formula II can be 3, 4 or 6. In still yet other embodiments, each R$^1$ of formula II can be methyl, and subscript m can be 3, 4 or 6.

In some other embodiments, the present invention provides compounds of formula IIa:

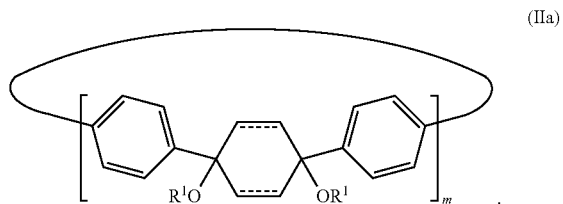

(IIa)

In formula IIa, the $R^1$ groups and subscript m can be as defined above. In addition, the dashed lines of formula IIa can optionally be a bond.

In another embodiment, the present invention provides compounds of formula IIb:

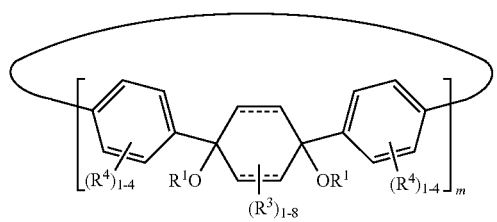

(IIb)

Each $R^3$ and $R^4$ can independently be hydrogen, halogen, $C_{1-6}$ alkyl, $C_{1-6}$ haloalkyl, $C_{1-6}$ heteroalkyl, $C_{2-6}$ alkenyl, $C_{2-6}$ alkynyl, $C_{1-6}$ haloalkoxy, $-OR^a$, $-C(O)R^a$, $-C(O)OR^a$, $-OC(O)R^a$, $-C(O)NR^aR^b$, $-NR^aR^b$, $-SR^a$, $-N(R^a)C(O)R^b$, $-N(R^a)C(O)OR^b$, $-N(R^a)C(O)NR^aR^b$, $-OP(O)(OR^a)_2$, $-S(O)_2OR^a$, $-S(O)_2NR^aR^b$, $-CN$, cycloalkyl, heterocycloalkyl, aryl or heteroaryl, wherein each $R^a$ and $R^b$ are as defined above. Alternatively, $R^3$ or $R^4$ groups on adjacent carbons can be combined with the atoms to which each is attached to form a cycloalkyl, heterocycloalkyl, aryl or heteroaryl. Moreover, each dashed line can optionally be a bond in formula IIb.

In some other embodiments, the present invention provides compounds of formula III:

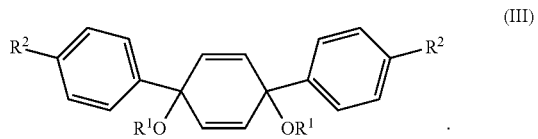

(III)

Each $R^1$ of formula III can be as defined above. Moreover, each $R^2$ can independently be a halogen or a boronate. Radical $R^2$ can also include a tri-alkyl tin. In yet other embodiments, the present invention provides compound of formula IIIa:

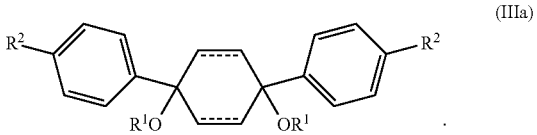

(IIIa)

Radicals $R^1$ and $R^2$ of formula IIIa are as described above. In addition, each dashed line of formula IIIa is optionally a bond. In still other embodiments, the present invention provides compounds of formula IIIb:

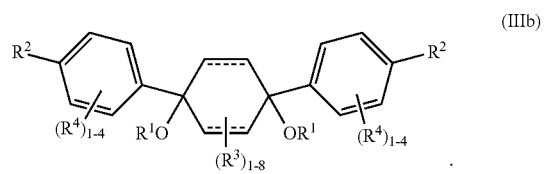

(IIIb)

Radicals $R^1$, $R^2$, $R^3$, $R^4$ and $R^5$ of formula IIIb are as described above. In addition, each dashed line of formula IIIa is optionally a bond.

Any boronate is useful in the compounds of the present invention. For example, some boronates useful in the compounds of the present invention include those of the following formula:

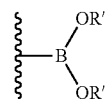

where each R' can independently be hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{1-6}$ haloalkoxy, cycloalkyl, heterocycloalkyl, aryl or heteroaryl. Alternatively, the two R' groups can be combined with the atoms to which each is attached to from a heterocycloalkyl. In some embodiments, the boronate is pinacol boronate (Bpin).

In other embodiments, each $R^1$ can be methyl and each $R^2$ can be iodo. In some other embodiments, each $R^1$ can be methyl, and each $R^2$ can be pinacol boronate.

The compounds of the present invention also include the salt forms and isomers thereof.

IV. Methods of Making the Compounds

The compounds of the present invention can be prepared by any method known in the art. For example, compounds of formula I can be prepared by coupling a 1,4-dihalophenyl compound with a benzoquinone to form the coupled compound 1,4-bis(4-halophenyl)cyclohexa-2,5-diene-1,4-diol. The 1,4-dihalophenyl compound can be substituted with any suitable $R^4$ group as described above. In some embodiments, the halogen is iodo or bromo. In other embodiments, the 1,4-dihalophenyl is 1,4-diiodophenyl. Likewise, the benzoquinone can be substituted with from 1 to 4 $R^3$ groups described above. Other benzoquinone groups suitable for the methods of the present invention include anthraquinone.

The 1,4-dihydroxy groups of the coupled compound can then be alkylated by any method known to one of skill in the art. The product of coupling the 1,4-dihalo phenyl and the benzoquinone is a compound of formula III, described above.

In some embodiments, the benzoquinone can be partially or fully saturated, i.e., a 1,4-cyclohex-2-ene-dione or 1,4-cyclohexadione, optionally substituted with 1-8 $R^3$ groups described above, to prepare a compound of formula IIIa or IIIb.

The halo groups of $R^2$ of the compounds of formula III, IIIa or IIIb can then be converted to boronates using any means known in the art. For example, replacing the halo group with a lithium anion followed by reaction with a borate ester will provide the desired boronate. In some embodiments, the borate ester is isopropyl pinacol borate, providing the product pinacol boronate.

Compounds of formulas II, IIa and IIb can be prepared a variety of methods known to one of skill in the art. For example, reacting the compounds of formula III, IIIa or IIIb where $R^2$ is halogen with compounds of formula III, IIIa or IIIb where $R^2$ is a boronate, using a metal catalyst under Suzuki coupling conditions can afford compounds of formulas II, IIa and IIb. Other methods of coupling the halogen and boronate compounds of formulas III, IIIa and IIIb are known to one of skill in the art, such as a Stille coupling or the dimerization of aryl halides. A Stille coupling involves an aryl tin and an aryl halide, using a suitable catalyst. For example, Richard C. Larock, *Comprehensive Organic Transformations* 1989, VCH Publishers, Inc., describes several coupling methods useful for making the compounds of the present invention.

The compounds of formula II and IIa are then aromatized using methods known to one of skill in the art. For example, the compounds of formula II can be aromatized using a reducing agent such as a one-electron reductant. One-electron reductants useful in the methods of the present invention include lithium naphthalenide. Other one-electron reductants useful in the methods of the present invention can be formed from an alkali metal such as Li, Na, K, Rb and Cs, and an aryl such as phenyl, naphthalene, and anthracene, among others.

The methods of the present invention can be practiced using a variety of suitable solvents, concentrations, temperatures, and other reactants. For examples, solvents useful in the methods of the present invention include, but are not limited to, tetrahydrofuran (THF), dioxane, toluene, benzene, methanol, ethanol, hexanes, diethylether, methylene chloride and chloroform. The methods of the present invention can be practiced at any suitable temperatures, such as from $-100°$ C. to $100°$ C.

In some embodiments, the present invention provides a method of preparing a compound of formula I, wherein each R of formula I can be hydrogen, and subscript n can be an integer of 6, 9, 12, 15, 18, 21, 24, 27 or 30. The method includes the step of contacting a reducing agent and a compound of formula II, wherein each $R^1$ of formula II can be hydrogen, $C_{1-6}$ alkyl, $C_{1-6}$ heteroalkyl, $C_{3-8}$ cycloalkyl, heterocycloalkyl, aryl or heteroaryl, and subscript m of formula II can be an integer from 2 to 10. Thus, the compound of formula I is prepared.

The reducing agent can be any agent that reduces the cyclohexadiene ring of formula II to form a phenylene ring. Suitable reducing agents include, but are not limited to one-electron reductants. In some embodiments, the reducing agent can be a one-electron reductant. In other embodiments, the reducing agent can include an alkali metal and an aryl group. Alkali metals include Li, Na, K, Rb and Cs. Aryl groups are defined above, and include, but are not limited to, phenyl, naphthyl, anthracene, and phenanthrene. In some other embodiments, the reducing agent includes a naphthalenide. In still other embodiments, the reducing agent is a one-electron reducing agent such as lithium naphthalenide. Other reducing agents are useful in the present invention.

The method of preparing compounds of formula I can also include the preparation of compounds of formula II, by contacting a benzoquinone and 1,4-diiodobenzene to prepare a compound of formula III. In formula III, each $R^1$ can be $C_{1-6}$ alkyl, and each $R^2$ can independently be iodo or a boronate. The method includes the step of contacting a plurality of compounds of formula III, wherein each $R^2$ is iodo for at least one compound of formula III and each $R^2$ is a boronate for at least one compound of formula III. Thus, the compound of formula II can be prepared.

Similarly, the present invention provides a method of preparing a compound of formula IIa. In formula IIa, each $R^1$ can independently be hydrogen, $C_{1-6}$ alkyl, $C_{1-6}$ heteroalkyl, $C_{3-8}$ cycloalkyl, heterocycloalkyl, aryl or heteroaryl. Each dashed line of formula IIa can optionally be a bond, and subscript m can be an integer from 2 to 10. The method of preparing a compound of formula IIa includes contacting a plurality of compounds of formula IIIa, where each $R^2$ can independently be a halogen or a boronate. Thus, the compound of formula IIa is prepared.

In some embodiments, the contacting step includes at least one compound of formula IIIa where each $R^2$ is a halogen and at least one compound of formula IIIa where each $R^2$ is a boronate. In other embodiments, the contacting step includes a plurality of compounds where one $R^2$ is a halogen and one $R^2$ is a boronate. Moreover, each dashed line of formula IIIa can be a bond.

V. Examples

General Experimental Details $^1$H NMR spectra were recorded at 500 MHz on a Bruker Biospin Avance II High Performance Spectrometer and were referenced to residual solvent peaks. $^{13}$C NMR spectra were recorded at 125 MHz on Bruker Biospin Avance II High Performance Spectrometer. Infrared spectra were recorded on a Varian 3100 FT-IR Spectrometer. UV/vis spectra were recorded using a Perkin Elmer Lambda 35 UV/Vis Spectrometer. Fluorescence spectra were recorded using a Jobin Yvon FluoroMax-4 Spectrofluorometer. All reagents were obtained commercially and purified prior to use. Tetrahydrofuran, diethyl ether, dichloromethane, and toluene were dried by filtration through alumina according to the methods described by Grubbs et al. (*Organometallics* 1996, 15, 1518-1520). Column chromatography was performed using a Biotage SP1 Flash Chromatography System. Thin layer chromatography (TLC) was performed on Whatman 250 µm layer silica gel plates. Developed plates were visualized using p-anisaldehyde, potassium permanganate, $I_2$ stains and UV light. All glassware was flame-dried and cooled under an inert atmosphere of nitrogen unless otherwise stated. Moisture sensitive reactions were carried out under an inert atmosphere of nitrogen using standard syringe/septa techniques.

Example 1

Preparation of 4

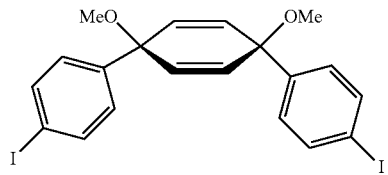

4

Diiodobenzene (31.3 g, 94.9 mmol, 2.05 equiv) was dissolved in 1 L of tetrahydrofuran and cooled to $-78°$ C. To this solution was added a 2.5 M solution of n-butyllithium in hexanes (41 mL, 102 mmol, 2.2 equiv) over 15 min. The reaction mixture was allowed to stir for 30 min. Benzoquinone (5.00 g, 46.3 mmol, 1 equiv) was then added to the reaction as a solid in three equal portions. The solution was stirred for 1.5 h and then added to 500 mL of water with stirring. The mixture was further diluted by the addition of 500 mL of diethyl ether. The biphasic mixture was allowed to stir for an additional 1 h and then the layers were separated. The aqueous layer was extracted with diethyl ether (3×300 mL) and the combined organic layers were washed with a saturated brine solution (300 mL). The organics were then dried over magnesium sulfate and concentrated in vacuo delivering the diol, which was carried forward without further purification.

To a dry 1-L round bottom flask was added 150 mL of tetrahydrofuran and 4.60 g of sodium hydride (116 mmol, 2.5 equiv). The mixture was then cooled to 0° C. and the crude diol was added as a solution in 50 mL of tetrahydrofuran. The mixture was stirred for 30 min whereupon neat methyl iodide (11.5 mL, 185 mmol, 4 equiv) was added. The mixture was allowed to warm to rt and stirred for an additional 16 h. The excess sodium hydride was then quenched by addition of 300 mL of water and this mixture was further diluted by addition of 200 mL of diethyl ether. The layers were separated and the aqueous layer was extracted with diethyl ether (3×150 mL). The combined organics were then washed with a saturated brine solution (150 mL) and dried over magnesium sulfate. The organics were then concentrated in vacuo delivering crude diiodide 4. The material was further purified by passing the crude mixture through a short plug of silica gel using 20% ethyl acetate/hexanes as the mobile phase. This technique was effective in removing tlc-baseline material that was problematic in recrystallization attempts. Concentration of the eluent then delivered a yellow solid that could be recrystallized from hot hexanes producing white, crystalline diiodide 4 (8.57 g, 34%): IR (neat) 2937, 2821, 1480, 1082, 818 cm$^{-1}$; $^1$H NMR (500 MHz, CDCl$_3$) δ 7.65 (d, J=9.0 Hz, 4H), 7.12 (d, J=9.0 Hz, 4H), 6.07 (s, 4H), 3.41 (s, 6H); $^{13}$C NMR (125 MHz, CDCl$_3$) δ 142.9, 137.4, 133.2, 127.9, 93.4, 74.4, 52.0; HRMS (FAB) m/z calcd for $C_{20}H_{18}I_2O_2(M)^+$ 543.9396. found 543.9406.

Example 2

Preparation of 5

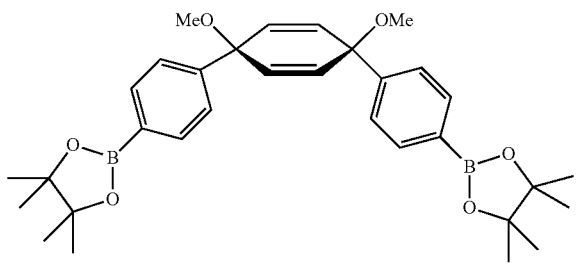

Diboronate 5.

Diiodide 4 (3.00 g, 5.51 mmol, 1 equiv) was dissolved in 60 mL of tetrahydrofuran and cooled to −78° C. To this solution was added a 2.5 M solution of n-butyllithium in hexanes (4.84 mL, 12.1 mmol, 2.2 equiv) over 2 min. Immediately after addition of the alkyl lithium reagent, neat isopropyl pinacol borate (4.50 mL, 22.0 mmol, 4 eq) was added rapidly and the solution was stirred for 30 min. Water (25 mL) was then added to the solution and the biphasic mixture was allowed to stir for 15 min at rt. The layers were then separated and the aqueous layer was extracted with ethyl acetate (3×15). The combined organic layers were washed with a saturated brine solution and then dried over magnesium sulfate. The organics were then concentrated in vacuo to deliver a yellow solid which could be further purified by recrystallization from hot ethyl acetate (2.46 g, 82%): IR (neat) 2978, 2361, 1610, 1361 cm$^{-1}$; $^1$H NMR (500 MHz, CDCl$_3$) δ 7.76 (d, J=8.3 Hz, 4H), 7.41 (d, J=8.3 Hz, 4H), 6.10 (s, 4H), 3.44 (s, 6H), 1.35 (s, 24H); $^{13}$C NMR (125 MHz, CDCl$_3$) δ 146.3, 134.9, 133.3, 125.3, 83.8, 75.0, 52.0, 24.8, C-B signal not observed; HRMS (FAB) m/z calcd for $C_{32}H_{42}B_2O_6(M)^+$ 544.3168. found 544.3183.

Example 3

Preparation of 6, 7 and 8

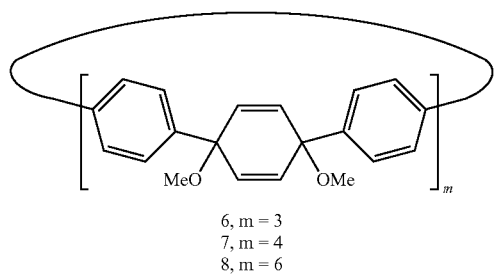

6, m = 3
7, m = 4
8, m = 6

Diiodide 4 (250 mg, 0.46 mmol, 1 equiv), diboronate 5 (250 mg, 0.46 mmol, 1 equiv), cesium carbonate (750 mg, 2.30 mmol, 5 equiv), and tetrakis(triphenylphosphine)palladium (50 mg, 0.046 mmol, 0.1 equiv) were dissolved in 33 mL of 10:1 toluene/methanol. The solution was degassed using standard freeze/pump/thaw technique (3×) and then heated to 80° C. for 16 h. After cooling to rt, the mixture was filtered through a short plug of Celite and then concentrated. The crude material was redissolved in dichloromethane and again filtered through a short plug of Celite. After concentration, the material was purified using a Biotage SP1 Flash Chromatography System (0 to 20% ethyl acetate/dichoromethane gradient). The macrocycles eluted in order of increasing size, delivering macrocycle 6 (4 mg, 2%), macrocycle 7 (51 mg, 10%), and macrocycle 8 (78 mg, 10%).

6: IR (neat) 2975, 1620, 1350 cm$^{-1}$; $^1$H NMR (500 MHz, CDCl$_3$) δ 7.47 (m, 24H), 6.17 (s, 12H), 3.48 (s, 18H); LRMS (FAB) m/z calcd for $C_{59}H_{51}O_5(M-CH_3O)^+$ 839. found 839.

7: IR (neat) 2975, 1621, 1082 cm$^{-1}$; $^1$H NMR (500 MHz, CDCl$_3$) δ 7.49 (m, 32H), 6.17 (s, 16H), 3.48 (s, 24H); $^{13}$C NMR (125 MHz, CDCl$_3$) δ 142.4, 140.0, 133.4, 127.1, 126.4, 74.7, 52.0; LRMS (FAB) m/z calcd for $C_{79}H_{69}O_7$ (M-CH$_3$O)$^+$ 1129. found 1129.

8: IR (neat) 2971, 1619, 1082, 818 cm$^{-1}$; $^1$H NMR (500 MHz, CDCl$_3$) δ 7.50 (m, 48H), 6.16 (s, 24H), 3.47 (s, 36H); $^{13}$C NMR (125 MHz, CDCl$_3$) δ 142.5, 139.9, 133.3, 127.1, 74.6, 52.0; LRMS (FAB) m/z calcd for $C_{119}H_{105}O_{11}$ (M-CH$_3$O)$^+$ 1709. found 1709.

Example 4

Preparation of 9

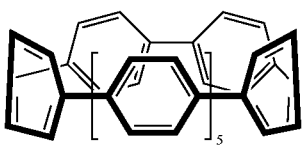

Lithium wire coated with mineral oil (35 mg, 5.0 mmol) was hammered into a sheet and cut into thin strips. The strips were then quickly rinsed with hexanes and added to a dry round bottom flask equipped with a glass stir bar. To this was added naphthalene (10 mg, 0.08 mmol) and 5 mL of tetrahydrofuran and the solution was cooled to 0° C. Within 15 min, the solution turned a dark green color and was then cooled to −78° C. To this solution was added macrocycle 7 (5 mg, 0.009 mmol) in 1 mL of tetrahydrofuran. The mixture was stirred for 15 min and then the excess lithium reagent was quenched by the addition of 3 mL of methanol. At this time, the excess lithium pieces were removed from the flask and set aside. The solution was then allowed to warm to rt and water (10 mL) and dichloromethane (10 mL) were added. The biphasic mixture was then separated and the aqueous layer was extracted with dichloromethane (3×5 mL). The combined organics were then dried over magnesium sulfate and concentrated in vacuo to deliver a yellow solid. This solid could be washed with hexanes in order to remove the excess naphthalene. Following this, the crude material was purified using a Biotage SP1 Flash Chromatography System (0 to 40% dichloromethane/hexanes gradient) delivering 1.8 mg (43%) of carbon nanohoop 9 delivering a yellowish-white, amorphous solid: IR (neat) 2923, 2852, 1484, 816 cm$^{-1}$; $^1$H NMR (500 MHz, CDCl$_3$) δ 7.53 (s, 24H); $^{13}$C NMR (125 MHz, CDCl$_3$) δ 137.9, 127.4; MALDI-TOF m/z calcd for $C_{54}H_{36}$ (M)$^+$ 684.2. found 684.2.

Example 5

Preparation of 10

The general procedure from above was followed delivering 4.2 mg (52%) of carbon nanohoop 10 as a white, amorphous solid: IR (neat) 2923, 2852, 1462, 812 cm$^{-1}$; $^1$H NMR (500 MHz, CDCl$_3$) δ 7.62 (s, 48H); $^{13}$C NMR (125 MHz, CDCl$_3$) δ 138.5, 127.3; MALDI-TOF m/z calcd for $C_{72}H_{48}$ (M)$^+$ 912.3. found 912.3.

Example 6

Preparation of 11

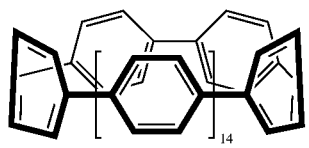

The general procedure from above was followed delivering 1.6 mg (36%) of carbon nanohoop 11 as a white, amorphous solid: IR (neat) 2922, 2851, 1462, 808 cm$^{-1}$; $^1$H NMR (500 MHz, CDCl$_3$) δ 7.71 (s, 72H); $^{13}$C NMR (125 MHz, CDCl$_3$) δ 139.0, 127.3; MALDI-TOF m/z calcd for $C_{108}H_{72}$ (M)$^+$ 1368. found 1368.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing a compound of formula I:

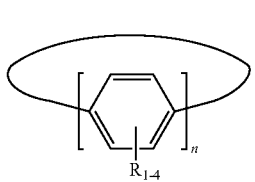

wherein
each R is hydrogen, and
subscript n is an integer selected from the group consisting of 6, 9, 12, 15, 18, 21, 24, 27 and 30,
the method comprising:
contacting a reducing agent and a compound of formula II:

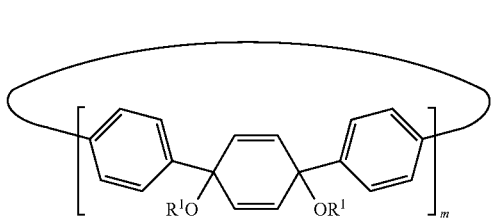

wherein
- each $R^1$ is independently selected from the group consisting of hydrogen, $C_{1-6}$ alkyl, $C_{1-6}$ heteroalkyl, $C_{3-8}$ cycloalkyl, heterocycloalkyl, aryl and heteroaryl, and
- subscript m is an integer from 2 to 10, thereby affording the compound of formula I.

2. The method of claim 1, wherein the reducing agent comprises a one-electron reductant.

3. The method of claim 1, wherein the reducing agent comprises an alkali metal and an aryl group.

4. The method of claim 1, wherein the reducing agent comprises a naphthalenide.

5. The method of claim 1, wherein the method further comprises:
contacting a benzoquinone and 1,4-diiodobenzene to prepare a compound of formula III:

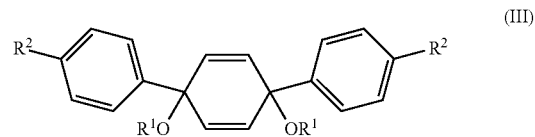

wherein
- each $R^1$ is $C_{1-6}$ alkyl,
- each $R^2$ is independently selected from the group consisting of iodo and a boronate; and
- contacting a plurality of compounds of formula III, wherein each $R^2$ is iodo for at least one compound of formula III and each $R^2$ is a boronate for at least one compound of formula III, to prepare a compound of formula II.

6. The method of claim 1, wherein subscript n is selected from the group consisting of 9, 12, 15, 18, 21, 24, 27, and 30, and wherein subscript m is an integer from 3 to 10.

* * * * *